(12) United States Patent
Agee

(10) Patent No.: US 11,220,473 B1
(45) Date of Patent: Jan. 11, 2022

(54) INTEGRATED GTL PROCESS

(71) Applicant: Emerging Fuels Technology, Inc., Tulsa, OK (US)

(72) Inventor: Kenneth L. Agee, Tulsa, OK (US)

(73) Assignee: Emerging Fuels Technology, Inc., Tulsa, OK (US)

( * ) Notice: Subject to any disclaimer, the term of this patent is extended or adjusted under 35 U.S.C. 154(b) by 0 days.

(21) Appl. No.: 17/179,924

(22) Filed: Feb. 19, 2021

(51) Int. Cl.
*C07C 29/151* (2006.01)
*C07C 1/04* (2006.01)
*C01B 3/24* (2006.01)
*C10G 2/00* (2006.01)

(52) U.S. Cl.
CPC ............ *C07C 29/1518* (2013.01); *C01B 3/24* (2013.01); *C07C 1/0485* (2013.01); *C10G 2/30* (2013.01); *C01B 2203/061* (2013.01); *C01B 2203/062* (2013.01); *C01B 2203/0833* (2013.01); *C01B 2203/1241* (2013.01)

(58) Field of Classification Search
CPC ..... C10G 2/30; C07C 29/1518; C07C 1/0485; C01B 3/24; C01B 2203/061; C01B 2203/0833; C01B 1203/1241; C01B 2203/062
See application file for complete search history.

(56) References Cited

U.S. PATENT DOCUMENTS

| | | |
|---|---|---|
| 5,177,114 A | 1/1993 | Van Dijk et al. |
| 5,245,110 A | 9/1993 | Van Dijk et al. |
| 5,733,941 A | 3/1998 | Waycuilis |
| 5,942,203 A | 8/1999 | Van Dijk et al. |
| 6,085,512 A | 7/2000 | Agee et al. |
| 6,130,259 A | 10/2000 | Waycuilis |
| 6,155,039 A | 12/2000 | Agee et al. |
| 6,172,124 B1 | 1/2001 | Wolflick et al. |
| 6,201,029 B1 | 3/2001 | Waycuilis |
| 6,265,453 B1 | 7/2001 | Kennedy |
| 6,277,894 B1 | 8/2001 | Agee et al. |
| 6,345,493 B1 | 2/2002 | Smith et al. |
| 6,669,744 B2 | 12/2003 | Allam et al. |
| 6,673,845 B2 | 1/2004 | Price |
| 6,794,417 B2 | 9/2004 | O'Beck et al. |
| 6,915,661 B2 | 7/2005 | Le Bot |
| 6,989,135 B2 | 1/2006 | Kennedy |
| 8,621,869 B2 | 1/2014 | Prabhu |
| 8,671,658 B2 | 3/2014 | Prabhu |
| 8,671,917 B2 | 3/2014 | Schnepel |
| 8,701,413 B2 | 4/2014 | Prabhu |
| 8,807,989 B2 | 8/2014 | Armstrong et al. |
| 8,844,473 B2 | 9/2014 | Schnepel et al. |
| 8,893,468 B2 | 11/2014 | Prabhu |
| 8,926,917 B2 | 1/2015 | Maslov |
| 8,980,192 B2 | 3/2015 | Maslov |
| 8,980,193 B2 | 3/2015 | Denison et al. |
| 9,017,618 B2 | 4/2015 | Maslov et al. |

(Continued)

*Primary Examiner* — Jafar F Parsa
(74) *Attorney, Agent, or Firm* — Head, Johnson, Kachigian & Wilkinson PC

(57) ABSTRACT

An integrated process for converting light hydrocarbon gases into products. Pre-packaged equipment such as a gas turbine and process compressors may be used to efficiently integrate the process. The gas turbine may provide all or a portion of the oxygen required in the process as compressed air. The turbine may be configured with a gradual oxidizer that can oxidize the process tail gas and drive the turbine, providing power for the process.

15 Claims, 1 Drawing Sheet

(56) References Cited

U.S. PATENT DOCUMENTS

| | | |
|---|---|---|
| 9,057,028 B2 | 6/2015 | Prabhu |
| 9,194,584 B2 | 11/2015 | Watts |
| 9,206,980 B2 | 12/2015 | Maslov |
| 9,234,660 B2 | 1/2016 | Armstrong et al. |
| 9,267,432 B2 | 2/2016 | Armstrong et al. |
| 9,273,606 B2 | 3/2016 | Hamrin et al. |
| 9,273,608 B2 | 3/2016 | Maslov |
| 9,279,364 B2 | 3/2016 | Hamrin et al. |
| 9,328,660 B2 | 5/2016 | Maslov |
| 9,328,916 B2 | 5/2016 | Lampe et al. |
| 9,347,664 B2 | 5/2016 | Lampe et al. |
| 9,353,946 B2 | 5/2016 | Hamrin et al. |
| 9,359,947 B2 | 6/2016 | Lampe et al. |
| 9,359,948 B2 | 6/2016 | Hamrin et al. |
| 9,371,993 B2 | 6/2016 | Armstrong |
| 9,381,484 B2 | 7/2016 | Armstrong et al. |
| 9,534,780 B2 | 1/2017 | Martin et al. |
| 9,567,903 B2 | 2/2017 | Armstrong et al. |
| 9,587,564 B2 | 3/2017 | Prabhu |
| 9,726,374 B2 | 8/2017 | Maslov et al. |
| 9,926,846 B2 | 3/2018 | Prabhu |
| 10,836,634 B1 | 11/2020 | Agee |
| 2002/0115731 A1 | 8/2002 | Price |
| 2002/0155061 A1 | 10/2002 | Prasad et al. |
| 2003/0119919 A1 | 6/2003 | Allam et al. |

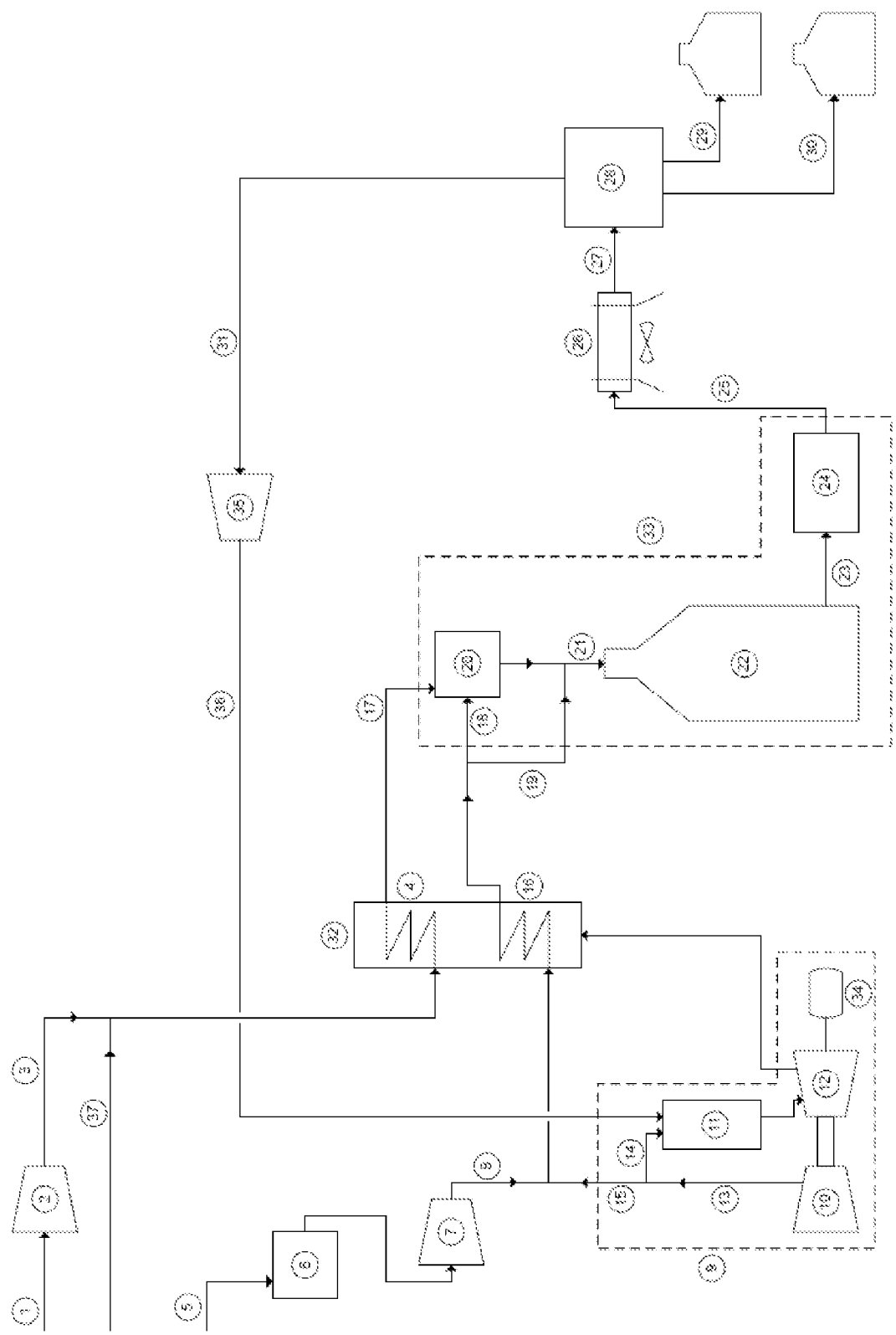

INTEGRATED GTL PROCESS

BACKGROUND OF THE INVENTION

Field of Invention

The present invention relates to an integrated gas to liquids process for the production of heavy hydrocarbon products from light gaseous hydrocarbons such as natural gas, associated gas, coal seam gas, landfill gas, or biogas.

Background

Various processes are known for the conversion of light hydrocarbon-containing gases into normally liquid products, such as methanol, higher alcohols, light olefins, and hydrocarbon fuels and chemicals, particularly paraffinic hydrocarbons. Such processes are directed at the objective of adding value to the feedstock by making a transportable, more valuable product such as diesel fuel, jet fuel, or chemicals such as base oils, solvents, or drilling fluids.

The Fischer-Tropsch process can be used to convert such light hydrocarbon gases into more valuable, easily transportable liquid hydrocarbon products and chemicals. The feedstock is first converted to synthesis gas comprising carbon monoxide and hydrogen. The synthesis gas is then converted to heavy hydrocarbon products over a Fischer-Tropsch catalyst. The heavy hydrocarbon products can be subjected to further workup or processing by hydroprocessing such as hydrocracking and/or hydroisomerization and distillation, resulting in, for example, a high yield of high-quality middle distillate products such as jet fuel or diesel fuel. The heavy hydrocarbon products can thereafter also be upgraded to chemical products such as solvents, drilling fluids, waxes, or lube base oils due to the high purity of the Fischer-Tropsch products.

Processes that convert light hydrocarbons to heavier hydrocarbon products generally have at least three steps: 1) conversion of the feedstock to synthesis gas comprising carbon monoxide and hydrogen; 2) conversion of the synthesis gas to heavy hydrocarbons via a Fischer-Tropsch reaction; and 3) hydroprocessing the heavy hydrocarbon product to produce one or more finished hydrocarbon products.

The efficiency and effectiveness of the subject process depends not only on the effectiveness of the three steps, but also on how the steps are integrated.

Based on the foregoing, it is desirable to provide an integrated gas to liquids process to efficiently and economically produce heavy hydrocarbon products from light gaseous hydrocarbons.

It is further desirable for such a process to eliminate the need for a fired heater by utilizing gas turbine exhaust heat.

SUMMARY OF THE INVENTION

In general, in a first aspect, the invention relates to a process for converting a light hydrocarbon gas feed stream into heavy hydrocarbon products, which process comprises: A) extracting compressed air from the compressor section of a gas turbine; B) pre-heating the compressed air stream to between 400 F and 1,100 F by exchange with exhaust gases from the gas turbine; C) providing a light hydrocarbon gas feed stream at a pressure substantially equivalent to the pressure of the pre-heated compressed air stream, where the light hydrocarbon gas feed stream is preheated to between 400 F and 1,100 F by exchange with exhaust gases from the gas turbine; D) converting the pre-heated compressed air stream and the light hydrocarbon gas feed stream into synthesis gas in a synthesis gas generation unit; E) converting the synthesis gas of step D into hydrocarbon products and water in a synthesis reactor; F) condensing and separating the hydrocarbon products and water of step E from light hydrocarbon gases and inert gases referred to as tail gas; and G) using tail gas from the synthesis reactor as fuel in a gradual oxidizer of the gas turbine, wherein the tail gas is inserted into a transition zone between the compressor discharge of the turbine and the inlet of the gradual oxidizer so that the tail gas and extracted air are kept separate by a backflow preventer.

The light hydrocarbon gas feed stream may comprise natural gas, associated gas, coal seam gas, landfill gas, biogas, or a combination thereof. The hydrocarbon products may comprise methanol, higher alcohols, Fischer Tropsch products, or a combination thereof.

The compressed air in step A may be further compressed to a pressure high enough that, after pressure losses through the synthesis gas generation unit and the synthesis reactor, the tail gas has a pressure high enough to flow into the gradual oxidizer of the gas turbine.

The synthesis gas generation unit may be operated at a pressure below the pressure of air extraction from the compressor section of the gas turbine and the tail gas compressed to a pressure required to flow into the gradual oxidizer of the gas turbine. The synthesis gas generation unit may comprise a partial oxidation reactor, an autothermal reformer reactor, or a combination thereof. The partial oxidation reactor may be catalytic or non-catalytic.

The choice of operating pressure may be up to the designer. With the turbine integrated configuration of the present invention, the tail gas pressure may be somewhat higher than the pressure in the gradual oxidizer so that the tail gas can flow into the gradual oxidizer. This pressure may be set by the discharge pressure of the compressor section of the turbine. As described above, the air extracted from the compressor may flow directly into the synthesis gas generator. Low pressure has advantages in the synthesis gas generation reactor as conversion efficiency is favored by low pressure. However, low pressure has disadvantage in the Fischer Tropsch reactor as higher pressure favors higher conversion and improved selectivity. The designer of a process employing the present invention must ultimately increase the pressure so that the tail gas after the synthesis reactor has enough pressure to flow into the gradual oxidizer. This requirement forces a decision to either compress the air after extraction of the turbine to high enough pressure to flow through the synthesis gas generation reactor and the synthesis reactor so that tail gas can flow into the gradual oxidizer, or compress the synthesis gas after the synthesis gas generator so that after product synthesis, the tail gas has adequate pressure to flow into the gradual oxidizer or compress the tail gas after product synthesis. There is no correct or preferred method and all three or any combination may be used. One advantage to further compression of the extracted air stream is that increasing the system pressure here involves lower volumes of gas compared to compressing the tail gas, and air compression is generally less expensive than synthesis gas compression.

The gas turbine may drive a power generator. The power generator may provide substantially all of the power required to drive the process. The tail gas may provide substantially all energy required to drive the gas turbine. Any excess tail gas above what is required to operate the gas turbine may be combusted in a duct burner or oxidized in a gradual oxidizer, in the exhaust of the gas turbine, or as a separate heater wherein the heat energy may be used in the process. The process may further comprise adding a small amount of supplemental fuel to the tail gas if the tail gas energy content is not adequate to operate the gas turbine at full power.

The synthesis reactor may produce synthesized water, and the process may further comprise using the synthesized water for water flood or fracking purposes or vaporizing the synthesized water in an exhaust of the gas turbine. The process may further comprise stripping the synthesized water to remove trace organics such as alcohols and organic acids before vaporizing the synthesized water in the exhaust of the gas turbine. Light hydrocarbon feed gas may be used to strip trace organics from the synthesized water.

The process may further comprise pre-heating a feed stream to a hydroprocessing unit by exchange with an exhaust of the gas turbine, the feed stream comprising the hydrocarbon products, and further hydroprocessing the heavy products.

BRIEF DESCRIPTION OF THE DRAWINGS

FIG. 1 illustrates a simple process diagram according to the present invention.

Other advantages and features will be apparent from the following description and from the claims.

DETAILED DESCRIPTION OF THE INVENTION

The embodiments discussed herein are merely illustrative of specific manners in which to make and use the invention and are not to be interpreted as limiting the scope of the instant invention.

While the invention has been described with a certain degree of particularity, it is to be noted that many modifications may be made in the details of the invention's construction and the arrangement of its components without departing from the spirit and scope of this disclosure. It is understood that the invention is not limited to the embodiments set forth herein for the purposes of example.

In general, in a first aspect, the invention relates to the use of pre-packaged systems including compressors and a gas turbine to efficiently and economically process the light hydrocarbon gases to produce heavy hydrocarbon products. Specifically, a gas turbine comprising an air compressor, a gradual oxidizer, and an expansion turbine may be used to provide a slipstream of air extracted from the compressor section of the gas turbine at elevated pressure to provide all or a portion of the oxygen needed to produce synthesis gas in a synthesis gas generation unit.

The synthesis gas generation unit may comprise any type of reactor known to one skilled in the art to make synthesis gas. A preferred system may combine partial oxidation and autothermal reforming, specifically catalytic partial oxidation and autothermal reforming. The air from the compressor section of the gas turbine may be further compressed if needed to the appropriate pressure required by the synthesis gas generation unit. If, for example, the air from the gas turbine compressor is at 150 psig and the synthesis gas generation unit is designed to operate at 300 psig, the air could be compressed to 300 psig in a booster compressor.

The oxygen concentration of the air may be enriched by adding an oxygen enriched stream into the process. This option adds complexity and cost to the process. In a preferred embodiment, the process uses only air as the source of oxygen in the process. When air is the source of oxygen, the process may produce a dilute tail gas that is difficult to combust. Perhaps this difficulty explains why turbine integrated gas-to-liquids applications have not been commercialized. With the nitrogen content of air, the tail gas btu content can drop to well below 100 btu/ft3. This btu content becomes difficult to combust and may limit the conversion level of the synthesis gas. If the conversion is limited to keep the tail gas btu content high enough to combust, the process yield, efficiency, and energy balance suffers. When the turbine is configured with a combustor, this problem can be solved by adding the complexity and cost of enriching the oxygen concentration so that the tail gas btu content is high enough for combustion at high conversion levels in the synthesis step, as provided in U.S. Pat. No. 10,836,634. While the process of the present invention may use oxygen enriched air to generate synthesis gas, the use of the gradual oxidizer allows for oxidation of the tail gas, even if the btu content drops well below 100 btu/ft3. This allows the air-only version of the process of the present invention to operate at very high synthesis conversion of 90% or more, which is not possible with a gas turbine integrated process where the turbine is configured with a combustor and where no oxygen enrichment is provided.

The gradual oxidizer is not part of any standard gas turbine and must be added to the turbine. It is generally only possible to add the gradual oxidizer to a turbine that is configured from the manufacturer with an external combustor. The gradual oxidizer replaces the external combustor and, for the process of the present invention, this addition must be further modified to allow for extraction of compressed air and injection of low btu tail gas from the process. Only a portion of the compressed air may be extracted. The balance of the compressed air may mix with the low btu fuel and provide the oxygen needed in the gradual oxidizer to oxidize the low btu gas without flame. The transition piece that allows for air extraction and low btu gas injection must be configured to avoid back mixing of the low btu gas so that it is not mixed with the extracted air. This may be done by injecting the low btu tail gas downstream of the air extraction nozzle and placing a back mix preventer between the two. The back mix preventer may be special piping designed to minimize back mixing, a check valve, or any other device known to one in the art.

Light hydrocarbon gas, such as natural gas, may also be compressed to a pressure required by the synthesis gas generation unit. The light hydrocarbon gas and air streams may be reacted in the synthesis gas generation unit to produce synthesis gas comprising carbon monoxide and hydrogen. Steam may also be added to the synthesis gas generation unit as needed to prevent soot production and to adjust the H2:CO ratio. Preferably, steam may be used very sparingly in the process, such as less than 1:1 steam to carbon, or less than 0.75:1 steam to carbon, or more preferably less than 0.5:1 steam to carbon.

Steam may be available from the waste heat boiler of the ATR at sufficient pressure to be used in the process and therefore it may not be necessary to use the high temperature gas turbine exhaust to make steam. The high temperature gas turbine exhaust may be used in the process of the present invention primarily for high temperature heating requirements, such as preheating the feed streams to the synthesis gas generation unit. It may also be used to preheat feed to a downstream hydrocracker or hydroprocessing unit. This is a small energy need but at high temperature, which normally requires a fired heater. Eliminating the need for a fired heater by utilizing the gas turbine exhaust heat is another objective of the present invention.

The synthesis gas produced in the synthesis gas generation unit may be reacted in a synthesis reactor such as a Fischer Tropsch reactor to produce heavy hydrocarbon products. This synthesis step could also comprise a methanol reactor or higher alcohol synthesis reactor. For discussion herein, a Fischer Tropsch reactor and catalyst may be used for the hydrocarbon synthesis step. The output of the Fischer Tropsch reactor may include heavy hydrocarbon products, water, and tail gas, which is the light non-condensable (at ambient temperature) gases.

The heavy hydrocarbon products and water may be condensed and removed and the tail gas comprising un-reacted synthesis gas (carbon monoxide and hydrogen), light hydrocarbons (methane, ethane and propane), and inert gases such as nitrogen and carbon dioxide may be provided to the gas turbine gradual oxidizer as fuel. In a preferred embodiment, substantially all of the fuel required by the gas turbine may be provided by this tail gas stream. The tail gas from the Fischer Tropsch reactor may contain significant amounts of nitrogen and therefore may have a very low btu content. The gas turbine gradual oxidizer will oxidize the low btu fuel without flame and the heat from the oxidation reactions will increase the gas temperature for expansion in the turbine. Examples of the gradual oxidizer are described in U.S. Pat. Nos. 8,980,193 and 9,328,660.

Any excess fuel that cannot be oxidized in the gas turbine may be combusted with a duct burner in the gas turbine exhaust or oxidized in another gradual oxidizer. If combusted, it may require addition of high btu gas to sustain a flame. The hot gas turbine exhaust may be used to preheat the compressed air stream and the feed hydrocarbon gas stream before going to the synthesis gas production unit. Optionally, burning or oxidizing excess tail gas in the gas turbine exhaust may make it possible to pre-heat the synthesis gas generation feed streams to a higher temperature, which may improve the efficiency of the synthesis gas generation unit. Ideally, the amount of light gaseous hydrocarbon that is used as feed gas may be at least enough so that the Fischer Tropsch tail gas energy content is adequate to meet the energy requirement of the gas turbine.

The water produced in the Fischer Tropsch reactor may be used for oil field operation such as for water flood or fracking. If there is not a use for the water, it may optionally be put into the exhaust of the gas turbine and vaporized. In this case, it may be desirable to first strip any organics such as alcohols and acids out of the water. Feed gas may optionally be used to strip the organics out of the water. These organic alcohols and acids may be collected and sold as a product or recycled as additional feed to the synthesis generation unit.

In a preferred embodiment, the gas turbine may produce power and the power produced may be adequate to drive the air compression and all additional power requirements for the entire process. Additional requirements for power may include, but are not limited to, pumps, air coolers, lighting, and controls.

As described herein, use may be made of pre-packaged equipment such as a gas turbine, air compressor, and natural gas compressor, especially a gas turbine modified with a gradual oxidizer and device to extract air and add low btu tail gas without back mixing to efficiently integrate the components of a gas to liquids process. The gas turbine may provide part or all of the air and air compression requirements, oxidation and utilization of a low btu tail gas, power to operate all compression and other components of the process, exhaust heat to preheat process streams including the feed gas and air sources, and disposal of produced water. Gas turbines may be available in a large range of configurations and sizes that can be modified and used to integrate the process of the present invention.

The process configuration in FIG. 1 describes a preferred embodiment of the present invention. A gaseous hydrocarbon feedstock 1 such as natural gas, associated gas, coal seam gas, landfill gas or biogas may be compressed in a compressor 2 to a pressure required by a synthesis gas generation unit 33, which may comprise a POX reactor 16 and an autothermal reformer 18. The compressed natural gas feed stream 3 may optionally be combined with steam 31, which may reduce the potential for soot formation and may provide adjustment to the H2:CO ratio, and then may be pre-heated in a coil 4 within a gas turbine exhaust duct 30. The pre-heated gaseous hydrocarbon 13 may be mixed with an oxygen containing stream 14 at the inlet of the POX reactor 16.

Compressed air 9 from a compressor 6 of a gas turbine unit 5 may be split into oxidation air 10 and extraction air 11. Extraction air 11 may provide all of the process air required by synthesis gas generation unit 33. If additional air is required, it may be provided with an additional ambient air compressor (not shown). The oxidation portion of the air 10 may go through a back flow preventer and may be allowed to mix with tail gas 29 and the extracted portion of the air 11 may be kept separate from the air/tail gas mixture 35 by backflow preventer 34. The compressed, extracted air stream 11 may be pre-heated in a coil 12 in the gas turbine exhaust duct 30 and split into stream 14, which may be mixed with the entire pre-heated gaseous hydrocarbon stream 13 and fed to the POX reactor 16, and stream 15, which may be combined with the outlet of the POX reactor 16.

The partially oxidized feed stream exiting POX reactor 16 may be mixed with additional air 15 and the combined stream 17 may be transferred to the autothermal reformer 18. Hot synthesis gas 19 may exit the autothermal reformer 18 and may be quench cooled in a waste heat boiler 20. Synthesis gas 21 may be further cooled in an air cooler 22 and transferred to a Fischer Tropsch reactor system 24 via line 23, where carbon monoxide and hydrogen in the synthesis gas 21 may be reacted and separated into products, which may include water 26, heavy hydrocarbons 25, and gases 27.

The tail gas stream 27, which may contain inert gases such as nitrogen and carbon dioxide and combustible gases such as hydrogen, carbon monoxide, methane, ethane, and propane, may be optionally compressed in a compressor 28 and transferred via line 29 to be oxidized in the gas turbine gradual oxidizer 7. Hot combustion gases from gradual oxidizer 7 may be expanded through an expansion turbine 8, generating energy to drive compressor 6 and additional energy, which may drive a power generator 32. The power generator 32 may be used to drive process compressors, such as compressor 2 and compressor 28.

Whereas the devices and methods have been described in relation to the drawings and claims, it should be understood that other and further modifications, apart from those shown or suggested herein, may be made within the spirit and scope of this invention.

What is claimed is:

1. A process for converting a light hydrocarbon gas feed stream into heavy hydrocarbon products, which process comprises:

A) extracting compressed air from a compressor section of a gas turbine to produce a compressed air stream;
B) pre-heating the compressed air stream to between 400 F and 1,100 F by exchange with exhaust gases from the gas turbine;
C) providing a light hydrocarbon gas feed stream at a pressure substantially equivalent to the pressure of the pre-heated compressed air stream, where the light hydrocarbon gas feed stream is preheated to between 400 F and 1,100 F by exchange with exhaust gases from the gas turbine;
D) converting the pre-heated compressed air stream and the light hydrocarbon gas feed stream into synthesis gas in a synthesis gas generation unit;
E) converting the synthesis gas of step D into hydrocarbon products and water in a synthesis reactor;
F) condensing and separating the hydrocarbon products and water of step E from light hydrocarbon gases and inert gases referred to as tail gas; and
G) using the tail gas from the synthesis reactor as fuel in a gradual oxidizer of the gas turbine, wherein the tail gas is inserted into a transition zone between the compressor discharge of the turbine and the inlet of the gradual oxidizer so that the tail gas and extracted air are kept separate by a backflow preventer.

2. The process of claim 1 wherein the light hydrocarbon gas feed stream comprises natural gas, associated gas, coal seam gas, landfill gas, biogas, or any combination thereof.

3. The process of claim 1 wherein the hydrocarbon products comprise methanol, higher alcohols, light olefins, hydrocarbon fuels, and chemicals.

4. The process of claim 1 wherein all or a portion of the air required by the process is extracted from the compressor section of the gas turbine.

5. The process of claim 1 wherein the synthesis gas generation unit comprises partial oxidation or autothermal reforming or a combination of the two.

6. The process of claim 5 wherein the partial oxidation is catalytic or non-catalytic.

7. The process of claim 1 wherein the tail gas is at a pressure below the pressure adequate to flow into the gradual oxidizer, such that the process further comprises boosting the pressure of the extracted air before synthesis gas generation, boosting the pressure of the synthesis gas before the synthesis reactor, boosting the pressure of the tail gas after the synthesis reactor, or any combination thereof.

8. The process of claim 1 wherein the gas turbine drives a power turbine that provides a substantial portion of the power required to drive components of the process.

9. The process of claim 1 wherein any excess tail gas above what is required to fuel the gas turbine is combusted in a duct burner or oxidized in a gradual oxidizer to provide additional process heat.

10. The process of claim 1 wherein supplemental fuel is added to the tail gas if the energy content of the tail gas is not adequate to operate the gas turbine at full power.

11. The process of claim 10 wherein synthesized water is used for water flood operation, or fracking or is vaporized in the exhaust of the gas turbine.

12. The process of claim 1 wherein the oxygen content of the extracted process air stream is enriched by adding a separate oxygen enriched stream into the process.

13. The process of claim 1 wherein the back flow preventer in the transition zone of claim 1 comprises piping configured with special nozzles designed to prevent back flow or a check valve.

14. The process of claim 1 wherein steam may be added to the light hydrocarbon gas stream to reduce soot formation in the synthesis gas generation unit and to adjust the H2:CO ratio.

15. The process of claim 1 wherein the high temperature exhaust of the gas turbine may be used to heat process streams including preheating products for hydroprocessing.

* * * * *